United States Patent

Shriver

(10) Patent No.: US 8,974,482 B2
(45) Date of Patent: Mar. 10, 2015

(54) DEVICE TO STEER INTO SUBINTIMAL FALSE LUMEN AND PARALLEL PARK IN TRUE LUMEN

(71) Applicant: Edgar Louis Shriver, Aventura, FL (US)

(72) Inventor: Edgar Louis Shriver, Aventura, FL (US)

( * ) Notice: Subject to any disclaimer, the term of this patent is extended or adjusted under 35 U.S.C. 154(b) by 0 days.

(21) Appl. No.: 13/694,690

(22) Filed: Dec. 21, 2012

(65) Prior Publication Data

US 2014/0180323 A1    Jun. 26, 2014

(51) Int. Cl.
| | |
|---|---|
| A61B 17/00 | (2006.01) |
| A61M 25/01 | (2006.01) |
| A61B 17/34 | (2006.01) |
| A61B 17/3207 | (2006.01) |
| A61M 25/10 | (2013.01) |
| A61B 17/22 | (2006.01) |

(52) U.S. Cl.
CPC ........ *A61M 25/0194* (2013.01); *A61B 17/3207* (2013.01); *A61B 17/3478* (2013.01); *A61M 25/1011* (2013.01); *A61M 25/104* (2013.01); *A61B 2017/003* (2013.01); *A61B 2017/22044* (2013.01); *A61B 2017/22094* (2013.01); *A61B 2017/22095* (2013.01); *A61M 2025/0197* (2013.01)
USPC .......................................................... 606/190

(58) Field of Classification Search
USPC ............... 604/93.01, 164.01, 164.03, 164.12, 604/164.13; 606/190, 191, 194
See application file for complete search history.

(56) References Cited

U.S. PATENT DOCUMENTS

| | | |
|---|---|---|
| 5,458,639 A | 10/1995 | Tsukashima et al. |
| 6,500,147 B2 | 12/2002 | Omaleki et al. |
| 6,511,458 B2 | 1/2003 | Milo et al. |
| 6,551,314 B1 | 4/2003 | Hill et al. |
| 6,554,795 B2 | 4/2003 | Bagaoisan et al. |
| 6,682,542 B2 | 1/2004 | Harkrider |
| 6,736,827 B1 | 5/2004 | McAndrew et al. |
| 7,169,160 B1 | 1/2007 | Middleman et al. |
| 7,179,270 B2 | 2/2007 | Makower |
| 7,713,215 B2 | 5/2010 | Shriver |
| 7,771,442 B2 | 8/2010 | Shriver |
| 8,241,311 B2 | 8/2012 | Ward et al. |
| 2004/0167554 A1 | 8/2004 | Simpson et al. |
| 2004/0181150 A1* | 9/2004 | Evans et al. .................... 600/433 |
| 2006/0079769 A1* | 4/2006 | Whiting et al. ............... 600/434 |
| 2007/0265596 A1 | 11/2007 | Jen et al. |
| 2008/0125748 A1* | 5/2008 | Patel ............................. 604/509 |
| 2008/0154172 A1 | 6/2008 | Mauch |
| 2008/0243065 A1 | 10/2008 | Rottenberg et al. |
| 2010/0274187 A1* | 10/2010 | Argentine .................. 604/96.01 |
| 2011/0208222 A1* | 8/2011 | Ljahnicky et al. ............ 606/159 |

* cited by examiner

*Primary Examiner* — Ashley Fishback

(57) ABSTRACT

A device for steering J-tip guidewire through true lumen of artery to puncture site where an occlusion abuts artery wall and stylet wire in lumen of J-tip guidewire provides axis for screwing it between intimal and medial layers of artery wall and stiffens it sufficiently to transform J-tip to loop that dissects a false lumen between intimal and medial layers around occlusion to its end where tamping balloons push aside intimal layer and occlusion so false lumen and true lumen coincide allowing intimal layer to be safely pierced by stylet wire allowing blood flow through previously occluded artery segment.

6 Claims, 3 Drawing Sheets

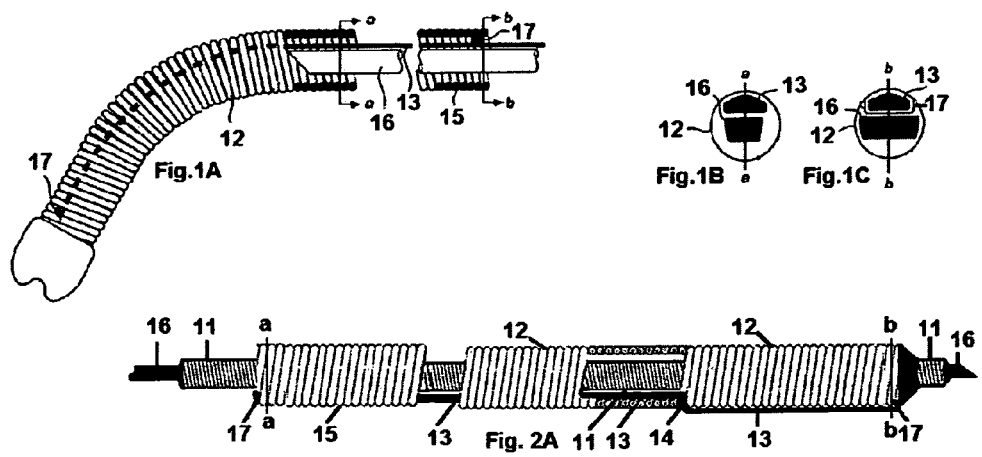
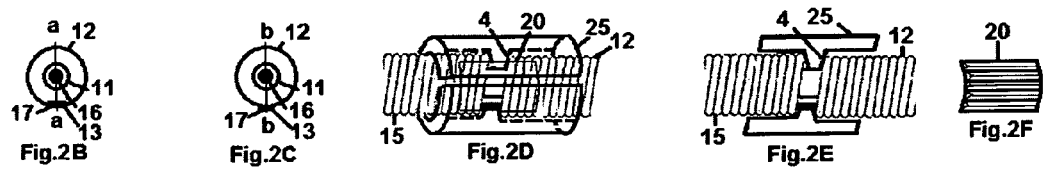
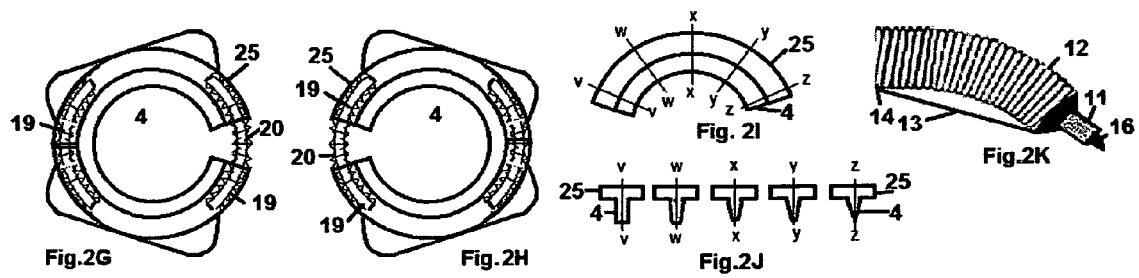
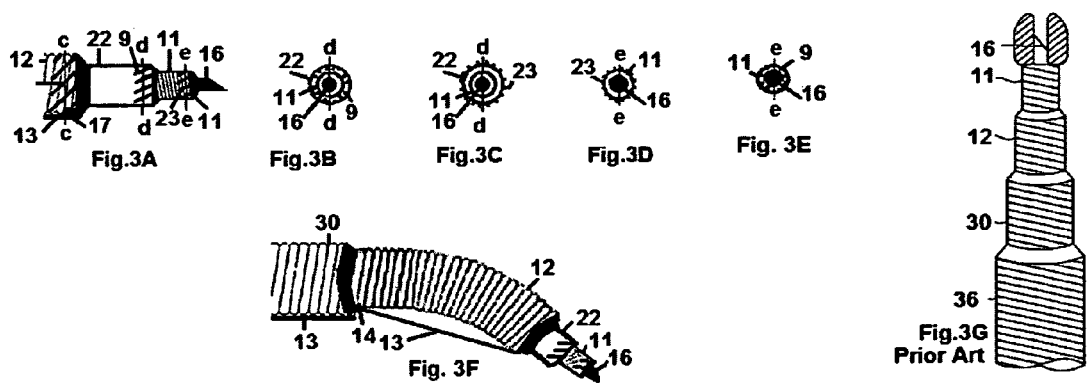

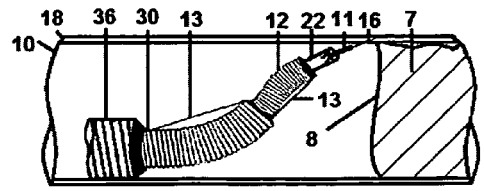
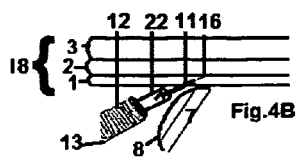
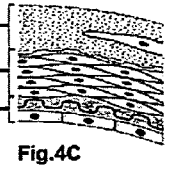
Fig.4A  Fig.4B  Fig.4C
Fig. 5
Fig. 6A
Fig. 6B
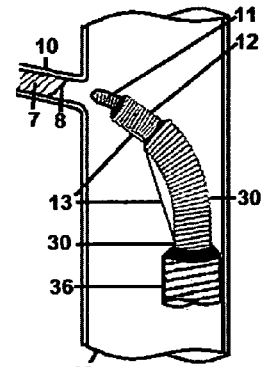
Fig.4D
Fig. 7
Fig. 8
Fig. 9A
Fig. 9B
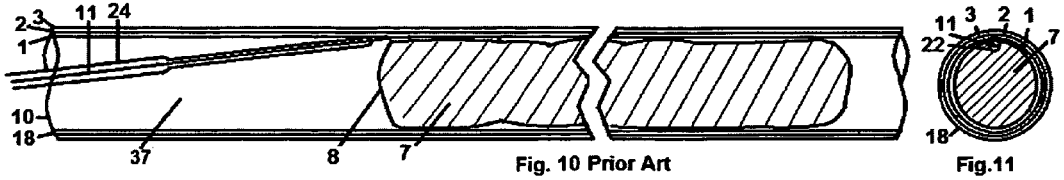
Fig. 10 Prior Art
Fig. 11 Prior Art
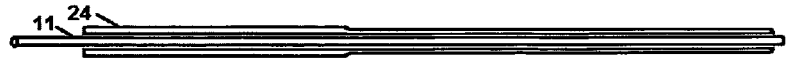
Fig. 12 Prior Art
Fig. 13A Prior Art

DEVICE TO STEER INTO SUBINTIMAL FALSE LUMEN AND PARALLEL PARK IN TRUE LUMEN

CROSS-REFERENCE TO RELATED APPLICATIONS

The device disclosed in U.S. Pat. No. 7,771,442 has the object of piercing and steering a guidewire in body tissue. The device disclosed here, by the same inventor, has the object of steering a guidewire within the lumen of a blood vessel and piercing tissue of vessel wall. The means described in the prior patent are not intended to accomplish the objects of the present application but the prior art has similarities that may require incorporation of some parts in present device.

FEDERALLY SPONSORED RESEARCH

Not Applicable

SEQUENCE LISTING OR PROGRAM

Not Applicable

BACKGROUND OF THE INVENTION

1. Field of the Invention

The field generally relates to making a passageway through or around an occlusion in a blood vessel, generally an artery. There are several types of prior art for creating a passageway by: 1 expanding a balloon in the center of an occlusion thus pushing it aside, 2 removing the occlusion through a process of grinding, scraping, freezing, lasering or other means, 3 placement of a bypass passageway adventitial to artery wall, or 4 placement of a false lumen between layers of artery wall to bypass occlusion and inflating balloons in false lumen to push inner layer of artery wall and occlusion to side of true lumen. Only the last named is the object of the present invention.

2. Prior Art

Prior Art References

| U.S. Patent/ Application Number | Year | Name |
| --- | --- | --- |
| 5,458,639 | 1995 October | Tsukashima et al. |
| 6,500,147 | 2002 December | Omaleki et al. |
| 6,511,458 | 2003 January | Milo et al. |
| 6,551,314 | 2003 April | Hill et al. |
| 6,554,795 | 2003 April | Bagaoisan et al. |
| 6,682,542 | 2004 January | Harkrider |
| 6,736,827 | 2004 May | McAndrew et al. |
| 7,169,160 | 2007 January | Middleman et al. |
| 2004/0167554 | 2004 | Simpson et al. |
| 7,179,270 | 2007 Feb. 20 | Mackower |
| 2007/0265596 | 2007 Nov. 15 | Jen et al. |
| 2008/0243065 | 2008 Oct. 02 | Rottenberg et al. |
| 2008/0154172 | 2008 Jun. 26 | Mauch |
| 7,713,215 | 2010 May 11 | Shriver |
| 7,771,422 | 2010 Aug. 10 | Shriver |
| 8,241,311 | 2012 Aug. 14 | Ward et al. |

3. Objects and Advantages

There is a subintimal (SI) technique for twisting a J-tip guidewire in a tapered catheter through a puncture site at the proximal cap of an occlusion in the true lumen of an artery and deliberately dissecting a false lumen between intimal and medial layers of the artery wall with the loop formed by the J-tip guidewire to bypasses the occlusion from its proximal cap to its distal cap. The J-tip guidewire pierces the intimal flap to re-enter the true lumen in a percentage of cases but prior art devices are used to find the direction in which the true lumen lies from the false lumen by ultrasound or orthogonal X-ray fluoroscopy in an additional 10-15% of cases. These prior art devices are marketed as Pioneer® and Outback®. While being successful with a percentage of cases, they are ineffective in an additional percentage of cases which varies but is 20% in some centers where they are used. Additionally, because they are of relatively large diameter they are limited to use in relatively large vessels, such femoral arteries and some popliteal arteries but are too large to be used in coronary arteries or in smaller vessels below-the-knee. These prior art devices use a hollow needle around the J-tip guidewire to pierce the intimal layer at an acute angle which dangerously points toward artery wall opposite. With prior art devices, after the true lumen is re-entered, a balloon is inflated repeatedly to tamp the intimal layer and occlusion aside in the true lumen so blood flows through the previously occluded segment of artery. If the device fails to re-enter true lumen surgery is the "bail-out" procedure required immediately to place a bypass graft around the occlusion.

The prior art device of US Pub. No. 2008/0243065, which is in clinical trials as OffRoad® finds the true lumen from the false lumen by a different means than those used by Pioneer® and Outback®. It describes a conical balloon with inverted neck on distal end that is inflated in a dissection between artery layers (false lumen) located in healthy tissue distal to the occlusion. The balloon catheter is acutely bent in direction of true lumen by inflating the conical balloon which pushes its large distal end with inverted neck toward true lumen while the smaller proximal end of conical balloon remains close to false lumen. The conical balloon is thus in the false lumen with its inverted end pointing toward true lumen. In one configuration a guidewire in catheter lumen is used to pierce intimal layer and enter the true lumen while in another configuration a hollow needle is introduced through the balloon catheter to pierce the intimal layer. Since the catheter is pointed toward the true lumen it is also pointed at the artery wall opposite with no means of limiting the distance the piercing component will travel. But whether or not opposite wall is injured, the healthy tissue in which balloon is inflated is injured and collateral vessels attached in that healthy tissue may bleed and clot which would be sufficient to terminate the percutaneous procedure and bail out to surgery. The acute bending the catheter is also a weakness, making lumen smaller and creating other complications that are addressed by alternative configurations that place a joint at bend or make bend of an especially flexible material. An alternative configuration of this prior art device uses a longer cylindrical balloon with inverted neck to make the hollow needle more parallel to longitudinal axis but this causes balloon catheter to be more sharply bent and the length of healthy tissue injured is even longer thus gaining little while making the balloon catheter weaker and more prone to failure by an even more acute bend. This prior art focuses on re-entry, stating only that guidewire in balloon catheter makes the dissection between layers, i.e. the false lumen.

Another prior art device for re-entry of true lumen from false lumen is described in U.S. Pat. No. 8,241,311. The invention limits itself to re-entry even more than the inverted neck balloon device does as it suggests use of a laser wire or radiofrequency electrode to bore the false lumen without describing how these alternatives achieve those objects or claiming them. It also suggests use of radiopaque elements to find the true lumen but does not claim them. It does claim a lower profile than the prior art Pioneer® and Outback® devices. It avoids the need for bulky means, such as ultrasound by simply extending a cutting blade from the side of the re-entry guidewire and circumferentially rotating the blade 360 degrees. Since this includes all possible directions it includes the direction the true lumen is in. If the blade is not sufficiently extended to completely sever the intimal layer with this circumferential maneuver, the device provides a balloon for enlarging the 360 degree opening thus splitting the intimal layer. But no balloons is provided for tamping aside the occlusion, rather a stent is prescribed for opening the lumen to allow blood to flow.

There is also prior art for a mechanism that limits distance hollow needle advances to prevent it from piercing wall opposite. The need for this type of mechanism and other described means of finding true lumen are eliminated with present device.

The present invention provides a means of steering a J-tip guidewire with a piercing stylet wire transluminally (through true lumen) to the puncture site where the stylet wire pierces the intimal layer, provides an axis of rotation for screw grooves that assist the entry of J-tip guidewire through intimal layer, stiffens J-tip enough to make it form the correct size loop that dissects a false lumen between layers of the artery wall and before entering healthy tissue inflates one or more balloons in false lumen to make longitudinal exes of false and true lumen approximately coincident or parallel. Thus stylet wire points straight ahead to pierce intimal layer rather than pointing dangerously at opposite wall. A plurality of balloons is used rather than only one balloon to quickly tamp aside the entire length of occlusion, wrapped in diseased section of intimal layer without injury to adjacent healthy tissue or pointing piercing instrument dangerously at opposite artery wall. Since this device does not use ultrasound or orthogonal X-ray fluoroscopy to "find" true lumen but uses one or more balloons to simply push false lumen into true lumen it is difficult to see how this device will fail to "find" the true lumen in some percentage of cases or. In addition, the profile of present device may be made small enough to be used in coronary arteries and those arteries below-the-knee, e.g. 1-2 mm. Further, the steering guidewire revealed for assisting operator in transluminally approaching hard-to-reach puncture sites may be of use as a substitute for various shaped guide catheters, e.g. Judkins, Amplatz, used to locate and enter the ostium of coronary arteries where they branch from the aorta.

The present invention avoids the disadvantages of prior art while providing advantages as described, in summary providing the following unique advantages over prior art:

1. Provides means of steering guidewire and stylet wire to puncture site which is point of entry into artery wall where occlusion abuts wall and makes entry difficult from certain angles;
2. Stylet wire that provides piercing means to aid entry of J-tip guidewire through intimal (innermost) layer of artery wall and also provides axis of rotation for J-tip guidewire and other elongated instruments that may have screw grooves or vanes for screwing through innermost layer of artery wall;
3. Stylet wire provides stiffening for J-tip guidewire to maintain loop in tip that is of correct size to dissect a false lumen between intimal and medial layers of artery wall;
4. Advancing catheter provides alternative means of stiffening guidewire to maintain correct size loop and may have screw grooves or vanes on its end for screwing through innermost layer of artery wall;
5. Multiple concentric guidewires of increasing diameter may be used to steer or to enlarge false lumen and relieve pressure on J-tip guidewire as is often encountered with long occlusions;
6. A tamping catheter with one fluid line for distal balloon located on distal end of tamping catheter and another fluid line for the plurality of short tamping balloons located proximal to distal balloon as short balloons provide more even force than does long balloons and thus are more efficient and less time consuming;
7. Tamping catheter may also be advanced to slightly increase size of false lumen and thus relieve pressure on guidewire loop in long occlusions;
8. Distal tamping balloon provides means of tamping from false lumen into true lumen in unhealthy tissue thus not injuring healthy tissue whereas prior art balloon expands in healthy tissue;
9. Distal tamping to enter true lumen from false lumen avoids the need for complex and expensive ultrasound or orthogonal X-Ray imaging used by prior art devices to find true lumen from false lumen,
10. Use of stylet wire in J-tip guidewire allows present device to be of smaller diameter than prior art devices and thus usable in coronary arteries and below-the-knee arteries where prior art large diameter devices cannot be used;
11. Using tamping balloons to find true lumen from false lumen by pushing against adventitial layer to push aside intimal layer and occlusion aligns stylet wire with longitudinal axis of true lumen thus stylet wire is not pointed at an angle that places opposite wall in danger of being pierced as do all prior art devices. This also avoids the need for a mechanism to limit distance piercing element travels as provided by one prior art device;
12. The profile of present device is smaller than that of prior art devices by an amount that allows its use in below-the-knee applications and in many coronary applications, none of which can be treated with the relatively large diameter prior art devices discussed above.
13. Present device avoids the need of prior art device to circumferentially rotate a cutting blade 360 degrees which must include cutting intimal layer between false lumen and true lumen while providing the low profile of this prior art device.

Accordingly, there is no prior art with the object or means of accomplishing the objects as effectively, safely, and with less injury, danger and in less time as with the device revealed here.

Atherosclerosis is a disease that afflicts about 20 million people in the United States, more than any other life threatening disease. The Greek word "athero" means "gruel" and "sclerosis" "hardening," so the disease is also known as "hardening of the arteries." Today this gruel or atheroma is often called "plaque," a deposit of cells, calcium, debris, and cholesterol in artery walls or in walls of conduits used as arteries. The occlusion narrows the artery lumen and the outermost or adventitial layer of the artery, which has about 80% of the strength of the wall, expands to compensate, but the net effect is that the lumen narrows. The plaque may rupture, cause blood clots, and/or calcify. The most extreme case is a chronic total occlusion (CTO of more than 99% occlusion for 3 months). An occlusion that narrows the artery to the point where it is incapable of delivering oxygen-carrying blood to muscles and organs beyond the occlusion requires intervention, surgical or percutaneous. There may or may not be symptoms or results from stress tests or EKG to indicate the need for intervention and a CTO is (presently) an indication for immediate surgical intervention. The arteries may be those of the heart or peripheral to the heart (usually legs). When the brain or heart is oxygen-deprived, death or impairment occurs rapidly. When muscles of the lower body are oxygen-deprived, death is slower but half die within 10 years. There may or may not be pain symptoms in the legs and gangrene may be the first clear indication with amputation or surgical intervention required to avoid death. Atherosclerosis may be treated by diet and drugs but patients often do not follow diets and the effects of tobacco smoke are irreversible even if the person stops smoking. So intervention is necessary in about 2 million cases in the US each year. About 75% of interventions are by percutaneous means rather than by surgical means as risk and debilitation are less. The gold standard treatment is a bypass graft placed by open surgery with its ends "grafted" to slits in the artery on each side of the occlusion thus carrying blood around it. The reason this is the gold standard is that a bypass graft remains functional about 7½ years on average until 50% of cases fail. This is much longer than the duration of percutaneous means but despite this advantage, bypass grafts require surgery that is risky and debilitating. A coronary artery bypass graft (CABG) starts with a sternotomy which splits the sternum and pulls apart the rib cage and usually continues with a heart lung machine for oxygenating and circulating blood through the body for about an hour while the heart is intentionally stopped. After a CABG procedure a patient is in intensive care for a day or more, in hospital for a week and has a long recovery at home. This is done to allow the surgeon's hands to get to the non-beating heart to place about 8 sutures on each end of each bypass graft (sometimes more than 3 grafts-as in a triple bypass procedure) and the rate at which a skilled surgeon can do this is about a minute per suture. A heart lung machine can be safely used for about an hour and a triple bypass would require 48 sutures or more. There are so-called "da Vinci" machines that can assist the surgeon's fingers to remain steady enough to place coronary bypasses through openings in the chest while the heart continues to beat, but this machine is expensive and applicable in a limited number of cases. Open surgery to place a bypass graft in the lower body is not as debilitating but is risky and involves a long recovery time in comparison to percutaneous entry through a skin puncture, which allows most patients to go home the next day with almost immediate recovery. The most common catheter-based method of intervention is to enter the body through a skin puncture in the groin where the femoral artery is close to the skin. After percutaneous entry with a hollow needle piercing both skin and artery, a guidewire is advanced through the needle and through the vasculature and then it enters the narrow occlusion rather than going around it. A balloon on a catheter is then advanced over the guidewire and into the occlusion where it is inflated to push aside the occlusion and thus open the artery. But the occlusion starts to close (re-stenose) when the balloon is removed. Balloons used alone result in the occlusion remaining open about 2½ years on average until 50% of cases close again, i.e., fail. To keep the occlusion propped open, stents were developed in the 1990s. Stents are wire mesh tubes that increase the length of time balloon treatments last in coronary artery applications to about 5 years until 50% fail. But in the longer arteries and occlusions of the legs, stents are likely to fracture so tend not to be used thus balloons are used alone.

The bypass graft for coronary arteries, which are generally less than 5 mm diameter, must be a vein, usually harvested from the patient's leg. It lasts about 7½ years on average until 50% of the bypass grafts need replacement. An artery of the leg is generally larger than 5 mm so the bypass graft around an occlusion in a leg artery can be made of artificial material. Blood flow in an artificial artery of 4 mm or less is too small for them to be of practical use. But flow is sufficient in some types of artificial graft tubes that minimize resistance and are of 5 mm or greater diameter so that they last almost 7½ years on average, i.e. until 50% of patients have experienced failed grafts. Therefore artificial bypass grafts are preferred in legs, but surgery is required to place them. Percutaneous treatments have largely replaced surgical bypass graft treatments but have not achieved the long duration of the bypass graft placed surgically. Therefore there is a continuing search for inventions that increase the duration of percutaneous treatments including those for placing a bypass graft percutaneously. This is in hope that a treatment means will be found that lasts 7½ years rather than the 2½ years for balloon angioplasty alone or for 5 years when a stent can be used. But so far no treatment means has been found that extends duration to greater than 2½ years except the stent that creates such a problem of fracturing that it is not used in long occlusions of the leg arteries. There is also the problem of the occlusion growing back through the open mesh in stents. This was partially dealt with in 2005 by placing a substance on the stent that eluted over time to resist that growth. But that drug has created other problems, like causing blood clots that sometimes get caught in an artery of the brain causing a stroke. Eluting stents are used as are bare stents, but generally only in short coronary applications. The fact that stents tend to fracture in the legs has given rise to alternatives called stent grafts and to complete removal of the occlusion rather than pushing it aside. Contrary to expectations, complete removal, by any of several methods, including scraping with a blade, laser, freezing, and a roto-rooter device, results in re-growth of the occlusion in a shorter time than by pushing it aside with a balloon. However, after such plaque removal, a stent graft may be placed with the intention of keeping the occlusion from growing back. Stent grafts are generally successful in preventing the occlusion from growing back through the graft tube but the occlusion tends to grow back around the ends generally requiring repeat treatment in 50% of cases in less than 2½ years, and thus providing no improvement over a balloon alone without using the stent graft. These stent grafts have included ePTFE and heparin bioactive surfaces to inhibit intimal hyperplasia and re-growth of the occlusion. But the re-growth around the ends makes the duration for stent grafts no longer or even shorter than the duration for balloons alone. Balloon treatments have largely replaced surgical bypass graft treatments but they have not achieved the long duration of the bypass graft placed surgically. Each year in the US there are about 310,000 coronary artery bypass grafts (CABG) and 178,000 bypass grafts in legs placed surgically while there are more than 1.7 million percutaneous interventions.

It may be recognized that a successful combination of the effectiveness of bypass graft duration and the safety of percutaneous delivery would replace currently used means that have only one, not both. Prior art by the present inventor and by other inventors has described devices for combining means of placing a bypass graft around occlusions in coronary arteries outside the artery wall as is done in CABG surgery with percutaneous entry. None of these devices has been proven by clinical trials that resulted in approval by the Food and Drug Agency (FDA) for use. This is not because the bypass graft did not provide the longer duration but generally because of the problem of graft failure or real or assumed problems one or more steps in the percutaneous process of placing the graft. For instance, doubts have often been expressed about whether these prior art devices can accomplish re-entry into the artery after creating a passageway outside the artery wall. There is no such doubt about another means of re-entry after bypassing the occlusion between layers of the artery wall rather going outside the artery wall. That process, subintimal angioplasty, was originally developed in 1988 for treating CTOs in which the occlusion has no opening that can be entered with a balloon. It was originally accomplished with a collection of commonly available general purpose devices. The procedure was not extensively used, possibly because it requires substantial skill to use the collection of devices and it is counterintuitive to intentionally dissect two layers of an artery wall. But specialized devices are now available to make the process easier and to increase the number of cases that can be successfully treated. Prior art percutaneous devices are able to exit the artery lumen at the point of an occlusion, force a guidewire loop between intimal and medial layers of artery wall and re-enter the artery lumen after creating a passageway or false lumen between those layers that passes around the occlusion. That is, the true lumen is re-entered from the false lumen, and this is accomplished in about 80% of cases where it is attempted. At least two such devices have been approved by the FDA and are in use today; another simpler device is in clinical trials. The invention revealed here is of this type with improvements and means of avoiding recognized problems with prior art devices as have been described and summarized previously.

The product of subintimal angioplasty is a segment of previously occluded artery in which the occlusion has been pushed aside wrapped in the intimal lining from the diseased section of artery. This product is similar to complete removal of the occlusion by means of freezing, lasering, scraping or existing devices and to pushing aside the occlusion by a balloon that can be used in cases that are not CTO. Aside from the fact that the subintimal (SI) procedure is the only way to treat the $\frac{1}{3}^{rd}$ of cases that are CTOs, it can be used for non-CTO cases. SI can be performed in less time than can complete removal and would be used in non-CTO cases if there were a means of treatment that used the product of SI to increase the duration of treatment to longer than 2½ years. The 2½ years would be comparable to but not superior to use of balloons alone in non-CTO cases. Therefore this would not be an advantage for non-CTO cases, but if the subintimal procedure can be combined with a graft tube that lasts as long as the 7½ years achieved by bypass grafts or even 5 years as achieved with stents (which tend to fracture in legs), or even somewhat longer than 2½ years it would benefit a large number of people. Since SI provides a segment of artery previously occluded there is currently a search for the kind of graft that will extend the duration. This search is relevant to the present invention but not part of the invention. Briefly, it may be noted that stent grafts, though successfully used for cases involving aneurysms, have not accomplished an improvement over the balloon alone in cases where there is an occlusion. Contouring stent graft ends has not solved the problem of occlusions growing back around the stent graft ends. Efforts also have been made to stabilize the connection at each end so there is no rubbing of graft ends and artery wall during pulsing, but no solution has been found. The present inventor is submitting a patent application for such a bypass graft but the present patent application reveals an improved means of producing the subintimal arteriotomy needed to place such a graft tube.

BRIEF DESCRIPTION OF THE DRAWINGS

FIG. 1A is side view of prior art which is a steering, piercing guidewire with handle, ribbon and stylet wire similar to steering guidewire 12 of present invention.

FIG. 1B is a cross-sectional view of prior art steering guidewire near distal end where stylet wire, biased during manufacture, causes device to bend and ribbon is also in lumen.

FIG. 1C is a cross-sectional view of prior art handle showing ribbon attachment of ribbon inside lumen and stylet wire in lumen.

FIG. 2A shows side view of a steering guidewire that has certain similarities to prior art described in FIG. 1 but provides a different means of steering by ribbon passing through adjacent wound wire coils. Also shown is a J-tip guidewire containing stylet wire.

FIG. 2B is a cross-sectional view of handle showing ribbon attachment of ribbon inside lumen.

FIG. 2C is a cross-sectional view showing ribbon attached on outside of steering guidewire.

FIG. 2D is an isometric view of clamp arcs located around the separation between handle and steering guidewire with the outline of a ribbed wafer.

FIG. 2E is a cross-sectional view of clamp arcs located around the separation between handle and steering guidewire.

FIG. 2F shows one ribbed wafer of two (the other being behind steering guidewire).

FIG. 2G shows the two halves of clamp arcs in one of the two extreme positions operator can place them in by squeezing the halves of arc clamp arcs.

FIG. 2H shows the two halves of clamp arcs in the other of two extreme positions in which operator can place them.

FIG. 2I is a view of clamp arc and tapered rib with cross-sections v-z marked.

FIG. 2J shows clamp arcs and tapered rib at cross sections v-z.

FIG. 2K is a side view of steering guidewire showing the result of operator pulling handle while holding steering catheter in place as may be done with assistance of clamp arcs.

FIG. 3A shows steering guidewire which has in its lumen an advancing catheter which is an alternative configuration made of a tube of polymer, and in the lumen of advancing catheter is J-tip guidewire being steered.

FIG. 3B shows cross-sectional view of screw grooves at cross-section d as an alternative configuration of advancing catheter.

FIG. 3C shows cross-sectional view of screw vanes at cross-section d as an alternative configuration of advancing catheter.

FIG. 3D shows cross-sectional view screw vanes at cross section e of J-tip guidewire.

FIG. 3E shows cross sectional view screw grooves at cross section e of J-tip guidewire.

FIG. 3F shows steering guidewire bent by ribbon to steer J-tip guidewire with stylet wire in its lumen in direction of bend.

FIG. 3G shows prior art whereby steering guidewire may be manufactured in larger sizes, such as steerable guidewire larger and large concentric guidewire and stacked concentrically.

FIG. 4A shows two concentric steerable guidewires, one of larger size, making a multi-directional curve to reach a puncture site where cap on occlusion abuts artery wall.

FIG. 4B shows artery wall composed of three layers and a generally convex cap on occlusion.

FIG. 4C is a cross-sectional view showing the different cellular structures of the layers of artery wall surrounding true lumen of artery.

FIG. 4D is a side view of concentric steering guidewires of larger size in the large aorta being transluminally steered to ostium of coronary artery thus replacing the type of guide catheter normally used for that function. Stylet wire is not yet extended.

FIG. 5 is a side view of alternative configuration of advancing catheter.

FIG. 6A is a side view of stylet wire.

FIG. 6B shows stylet wire retracted in J-tip guidewire by the amount needed to form a loop of appropriate size for dissecting between layers of artery wall FIG. 7 shows stylet wire retracted in J-tip guidewire by more than the amount needed to form a loop of appropriate size in J-tip guidewire. Also shown is alternative configuration of advancing catheter which is positioned to form proper loop size.

FIG. 8 shows tamping catheter with distal tamping balloon located on distal end and a plurality of tamping balloons located proximal to distal tamping balloon.

FIG. 9A shows the alternative configuration of concentrically assembled tamping catheter, advancing catheter, J-tip guidewire and stylet wire.

FIG. 9B shows the alternative configuration of concentrically assembled tamping catheter, J-tip guidewire and stylet wire without advancing catheter.

FIG. 10 shows artery with occlusion, cap and 3 layers of artery wall with prior art of conventional catheter and J-tip guidewire.

FIG. 11 is a cross-sectional view of what is shown as a side view in FIG. 10.

FIG. 12 is a more detailed view of J-tip guidewire in conventional catheter to more clearly shows the thicker and thinner portions.

KEY

Figure 13B:
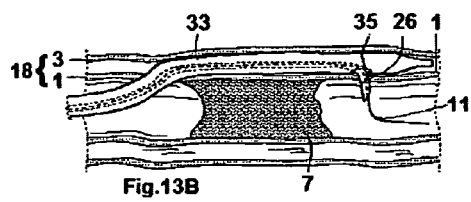
FIG. 13B shows the means of re-entering true lumen from false lumen used in prior art.
Figure 13F:
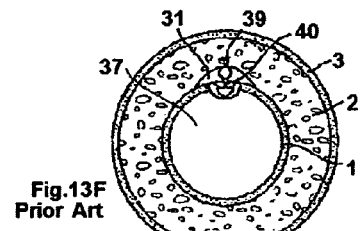
FIG. 13F is a cross-sectional view of prior art cutting blade 39 and re-entry guidewire between layer 1 and layer 3 of artery 10 with an arrow showing how a circumferential cut will be made.
Figure 13E:
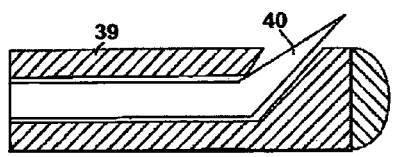
FIG. 13E is a side view of prior art cutting blade extended from re-entry guidewire.

1. Intimal layer
2. Medial layer
3. Adventitial layer
4. Tapered nib
5. Tamping balloons
6. Steerable guidewire
7. Occlusion
8. Occlusion cap
9. Screw grooves
10. Artery
11. J-tip guidewire
12. Steering guidewire
13. Ribbon
14. Ribbon exit
15. Handle
16. Stylet wire
17. Ribbon attachment
18. Artery wall
19. Ribbed receiver
20. Ribbed wafer
21. Inverted neck balloon prior art
22. Advancing catheter
23. Screw vanes
24. Conventional catheter prior art
25. Clamp arcs
26. Hollow needle prior art
27. Bent catheter prior art
28. Inverted neck prior art
29. Puncture site
30. Steerable guidewire larger
31. False lumen
32. Tamping catheter
33. Covering sheath prior art
34. Distal tamping balloon
35. Side opening prior art
36. Large concentric guidewire
37. True lumen
38. Balloon catheter prior art
39. Re-entry guidewire prior art
40. Cutting blade

DETAILED DESCRIPTION OF THE INVENTION

Having thus described the figures, methods in accordance with the present invention are now described with reference thereto. It should be understood that steps described for each process may be omitted or the order changed or performed simultaneously without deviating from the spirit or scope of the invention. The following description should be read with reference to the drawings, in which the elements in different drawings are numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practices regarding processes and materials. Those skilled in the art will recognize that many of the examples provided have suitable alternatives in materials, manufacturing processes and specific configurations which may be utilized now and in the future to produce equivalent means.

FIGS. 1A-C show side and cross-sectional views of prior art (by present inventor) for a steering, piercing guidewire 12 which, like most guidewires, is manufactured by winding flexible, resilient wire such as stainless steel or nickel-titanium alloy on a mandrel to produce a tube of wound wire having a distal end a proximal end and lumen therebetween, with lumen diameter equal to diameter of mandrel and outside diameter equal to 2 times diameter of wire plus diameter of mandrel. Thus a guidewire of about 0.035 inches OD has an ID of 0.017 when 0.009 inch wire is used to wind on a mandrel of about 0.017 inch diameter. Handle 15 is a short length 15 of same characteristics but separate from steering guidewire 12 which may be made by cutting wire near proximal end of steering guidewire 12. The lumen of steering guidewire 12 and lumen of handle 15 contain stylet wire 16 and ribbon 13, both of flexible resilient material such as stainless steel and having a distal end and a proximal end. Ribbon 15 is attached at ribbon attachment 17 in lumen on proximal end in at ribbon attachment 17 in lumen of handle 15 lumen and on distal end in lumen at distal end of steering guidewire 12 thus keeping handle 15 in contact with steering guidewire 12. Distal end of stylet wire 16 is sharp. Stylet wire 16 can be moved by operator to extend sharp distal end past distal end of steering guidewire 12 or to be at any point proximal to distal end of steering guidewire 12. Stylet wire 16 is biased during manufacture on distal end, thus when advanced to or slightly beyond distal end of steering guidewire 12, stylet wire 16 bends guidewire 12 in the curved shape shown. This bend tends to be counteracted by operator pulling handle 15 which shortens the length of ribbon 13 in lumen of steering guidewire 12 thus causing curved portion of steering guidewire 12 to straighten and this is the steering means for prior art steering guidewire 12.

FIG. 2A is a side view of an alternative configuration of steering guidewire 12 as revealed in this application that has certain similarities to prior art described in FIG. 1, but provides a different means of steering. Steering guidewire 12 may be manufactured by various methods and materials such as stainless steel, nickel titanium compounds and such methods as winding wire on a mandrel or laser cutting a spiral or slots in a hypotube. For consistency in description, but not intended to limit the guidewires method of manufacture or material, the conventional coil of wire as manufactured on a mandrel will be described and shown in figures. Ribbon 13 is attached on its proximal end inside lumen of handle 15 at ribbon attachment 17, and passes from there through lumen of steering guidewire 12 to exit lumen between adjacent coils at ribbon exit 14 and then continues distally outside steering guidewire 12 to be attached at ribbon attachment 17 on distal end of steering guidewire 12. Stylet wire 15 and ribbon 13 keep handle 15 aligned with and contiguous to steering guidewire 12. When operator pulls handle 15 while holding steering guidewire 12 in place this increases the separation between handle 15 and steering guidewire 12 causing ribbon 13 to be slightly shorter within steering guidewire 12 and thus also shorter in the section of guidewire 12 between ribbon exit 14 and ribbon attachment 17 thereby causing that section to bend as shown in FIG. 2K. This section of ribbon 13 constitutes a shorter chord on the arc of the section of steering guidewire 12 between ribbon exit 14 and ribbon attachment 17 than when handle 15 is not pulled, thus providing a different means of steering guidewire 12 than that used in prior art shown in FIG. 1A-C. Also shown in FIG. 2A is J-tip guidewire 11 with lumen containing stylet wire 16 that are being steered by steering guidewire 12. J-tip guidewire 11 is made in the usual way that guidewires are wound on a mandrel with a distal and proximal end with lumen therebetween but the tip on distal end is biased in a J-shape. Or it may be manufactured by other methods, such as laser cutting a spiral or cutting a series of slots in a metal hypotube. Outside diameter of J-tip guidewire may be about 0.035 inches or as small as 0.017 inches. This size is 1-2 mm diameter and sufficiently small to be used in most coronary applications and below-the-knee applications even when enclosed in a larger tamping catheter, advancing catheter or steering guidewire. Stylet wire 16 is a flexible wire of material such as stainless steel with a distal end a proximal end and straight shape (not biased) with sharp point on distal end. In this figure the bias of J-tip guidewire 11 is not seen because the tip is only slightly extended beyond distal end of steering guidewire 12 and stylet wire 16 in lumen being straight thus tends to straighten J-tip guidewire 11 when it is in lumen as shown. Stylet wire 16 in J-tip guidewire 11 is an alternative configuration for stiffening J-tip guidewire to maintain the correct size loop that J-tip assumes to creating false lumen 31 in artery wall 18 but serves other functions as well. Steering guidewire 12 is an alternative configuration for steering J-tip guidewire 11 and stylet wire 16 to intimal puncture site 29 of artery wall 18 as shown in FIGS. 4A and B. The alternative configuration is to use no means of steering to puncture site. This is the presently used means which is known to be difficult under certain conditions that may prevail in particular cases.

FIG. 2B is a cross-section view that shows ribbon 13 attached at ribbon attachment 17 inside lumen of handle 15 and stylet wire 16 in lumen of J-tip guidewire 11 inside lumen of steering guidewire 12.

FIG. 2C is a cross-section view that shows ribbon 13 attached at ribbon attachment 17 at distal end, and outside of steering guidewire 12 with stylet wire 16 in lumen of J-tip guidewire 11 inside lumen of steering guidewire 12.

FIG. 2D is an isometric view and FIG. 2E is a cross-sectional view of an alternative configuration of clamp arcs 25 located around the separation between handle 15 and guidewire 12. Clamp arcs 25 are made of metal such as stainless steel in the shape of a ring of approximately rectangular shape in cross-section with width greater than thickness, flat on all sides except for tapered protrusion on inside circumference. The protrusion is tapered nib 4 shown protruding between handle 15 and steering guidewire 12. Tapered nib 4 varies in width to keep handle 15 separated from steering catheter 12 by a varying amount that is a function of its tapered thickness and the position of the two halves of clamp arcs 25 to which operator rotationally shifts them, as will be described in connection with FIGS. 2I and J. Operator observes the amount of bend at distal end of steering guidewire 12 while rotationally squeezing the halves of clamp arcs 25 to obtain the desired amount of separation and lets go of clamp arcs 25 when the desired amount of bend is achieved. Clamp arcs 25 remain locked with tapered nib 4 maintaining that separation until operator again squeezes clamp arcs 25.

FIG. 2F shows one ribbed wafer 20 of two (the other being located behind steering guidewire 12) which is also shown as an outline in FIG. 2D. Each ribbed wafer 20 is made of a relatively inflexible, strong material such as stainless steel or a polymer shaped like an approximately square thin wafer that is made in a zigzag pattern such as found on an antique manual wash board.

FIGS. 2G and H show the two halves of clamp arcs 25 in the two extreme positions operator can place them by squeezing the halves of arc clamp 25 in a clockwise or counterclockwise direction. There is a gap between adjacent ends of the two halves of arc clamp 25 because each "half" is made to have slightly less than 180 degrees of circumference. Of course operator can choose any point between the extremes to obtain the amount of separation and thus amount of bending desired. Each ribbed wafer 20 is partially located in two adjacent ribbed receivers 19 that are zigzag shaped cavities located in the ends of adjacent halves of clamp arcs 25. The cavities are made in a zigzag shape that constitutes a series of ribs which match the shape of zigzag ribs on each ribbed wafer 20. The ribs engage to hold the halves of clamp arc 25 together wherever operator places the halves until operator changes that location which is readily done by squeezing the two halves of clamp arcs 25 to overcome the locked position.

FIGS. 2G and H show the two halves of clamp arcs 25 in the two extreme positions operator can place them by squeezing the halves of arc clamp 25. Ribbed wafers 4 are seen in ribbed cavities 19 holding two halves of clamp arcs 25 together and locked at whatever rotational angle operator places them.

FIG. 2I shows on half of clamp arc 25 with tapered nib 4 as a protrusion on inner circumference. All halves are shaped the same way so only one is shown with cross-sections v, w, x, y, and z.

FIG. 2J shows the shape of nib 4 at successive cross-sections, v, w, x, y, and z to which operator can turn halves of clamp arc 25 by squeezing. The shape of tapered nib 4 continually changes from wide to narrow around inside circumference of clamp arcs 25. This causes the separation distance to change as operator rotationally squeezes halves of clamping arc 25 from position shown in FIG. 2G to that shown in FIG. 2H thus placing a narrow protrusion of tapered nib 4 at one extreme and a wide protrusion of tapered nib 4 at the other extreme position.

FIG. 2K is a side view of steering guidewire 12 showing the result of operator pulling handle 15 while holding steering catheter 12 in place. This may be done with the assistance of alternative configuration of clamp arcs 25 as previously specified. Steering guidewire 12 can be used to steer any longitudinal object or objects in its lumen in the direction it is bent. In this figure the lumen of steering guidewire 12 has J-tip guidewire 11 and in its lumen is stylet wire 16.

FIG. 3A shows steering guidewire 12 which has in its lumen advancing catheter 22 which is an alternative configuration made of a tube of polymer, and in the lumen of advancing catheter 22 is J-tip guidewire 11 with stylet wire 16 in its lumen. When advancing, catheter 22 is used as an alternative combination configuration to stiffen J-tip guidewire 11, and it has OD slidably smaller than diameter of lumen of steering guidewire 12 and ID slidably larger than OD of J-tip guidewire 11. Two other alternative configurations are shown here as screw grooves 9 or screw vanes 23 on distal ends of steering guidewire 12, advancing catheter 22, and J-tip guidewire 11. The side view in FIGS. 3A and 3F uses diagonal lines which have the same appearance whether they represent screw grooves 9 or alternative configuration of screw vanes 23. Either assists the screwing of distal ends into intimal puncture site 29 which is punctured by stylet wire 16 in artery wall 18 as shown in FIGS. 4A and B. It is not known if operators will want to introduce steering guidewire 12 into artery wall 18 but there is a possibility that it would provide a means of reducing pressure on advancing catheter 22 at distal locations so it is shown here in alternative configuration with screw grooves 9 and screw vanes 23.

FIGS. 3B-E show cross-sectional views of alternative configurations that are screw grooves 9 or screw vanes 23 at cross sections d and e. Screw grooves 9 are in the shape of grooves between threads on a screw and screw vanes 23 are in the shape of threads between grooves on a screw.

FIG. 3F shows alternative configurations of advancing catheter 22 and steerable guidewire larger 30. Steerable guidewire larger 30 is the same as steerable guidewire 12 but of larger size such that lumen of steerable guidewire larger 30 contains steerable guidewire 12 thus providing two directions of bending bends for more precise steering. The alternative configuration shown in FIGS. 2A, B, C and G contain no advancing catheter 22 as stylet wire 16 supplies the stiffening of J-tip guidewire 11 that advancing catheter 22 provides when it is present. Such stiffening is needed for J-tip guidewire 11 to form the proper size loop for dissecting false lumen 31 between intimal layer 1 and medial layer 2 of artery wall 18 as shown in prior art in FIG. 13A and as an alternative configuration of present device in FIG. 14.

FIG. 3G shows prior art (by present inventor) whereby steering guidewire 12 may be manufactured in larger sizes, such as steerable guidewire larger 30 and large concentric guidewire 36 and that they may be stacked concentrically. Concentric stacking allows multi-dimensional steering, piercing tissue when stylet wire is advanced and increasing diameter of passage through tissue. In prior art this type of device is intended for use when creating an increasingly large passageway around an occlusion on the adventitial side of artery wall rather than within artery wall as is the intended use of present device. In prior art the increasingly large adventitial passageway is made through tissue in the fashion of an inchworm's movement with a short distance of piercing by the stylet wire followed by advancing each concentric guidewire which stiffens the base from which stylet wire is advanced another short distance in the direction desired. The stylet wire must re-enter artery wall after occlusion has been bypassed and this is difficult to accomplish. The invention revealed here is intended as a means of creating the passageway in the artery wall and re-entering true lumen of artery by a simpler, less difficult means but since certain similarities between this prior art and present device exist it is incorporated in part in the present specification.

FIG. 4A shows two concentric steerable guidewires, one of larger size, making a multi-directional curve to reach a puncture site on artery wall 18 where occlusion 7 has occlusion cap 8 which may be convex, concave or a combination in different cases. When occlusion cap 8 is convex it is somewhat easier to enter artery wall 18 at intimal puncture site 29 which is at the intersection of cap 8 and artery wall 18 and more difficult when occlusion cap 8 is other than convex. It may make entry easier at intimal puncture 29 if steerable guidewire 12 is used or if additional steerable guidewires of increased size labeled as steerable guidewire larger 30 and large concentric guidewire 36 are used in combination for more precision as shown. J-tip guidewire 11 is manufactured with a J-tip which will curve into a loop when advanced a short distance beyond advancing catheter 22 in tissue such as found between layers of an artery wall. For this loop to remain the correct size it must be stiffened at a short distance proximally from loop. This has been done in prior art by conventional catheter 24 as shown in FIGS. 10, 11 12 and 13A. In present device the stiffening may be provided by either of two alternative configurations, one being advancing catheter 22 the other being stylet wire 16. In FIG. 4A both are shown because stylet wire 16 has other functions than stiffening J-tip guidewire 12 to form the proper size loop. Stylet wire 16 is slidably smaller than and located within the inside diameter of J-tip guidewire 11 where it may be advanced beyond or withdrawn any distance from distal end of J-tip guidewire 11. It is shown here performing the functions of piercing at intimal puncture site 29 and providing an axis of rotation for screwing components such as advancing catheter 22 through intimal puncture site 29.

FIG. 4B shows artery wall 18 composed of layer 1, layer 2, and layer 3. It also shows a generally convex occlusion cap 8 on occlusion 7. Stylet wire 16 is shown slightly extended beyond J-tip guidewire 11. Stylet wire 16 is slidably smaller than and located within inside diameter of J-tip guidewire 11. This type of guidewire is generally used for percutaneous subintimal procedures and has characteristics to be further described with the aid of FIG. 7. Advancing catheter 22 is also shown here and it will be further described with the aid of other figures.

FIG. 4C is a cross-sectional view showing the different cellular structures of the layers of artery wall 18 surrounding true lumen 37 of artery 10. The innermost is intimal layer 1, the middle is medial layer 2 and the outermost is adventitial layer 3. Adventitial layer 3 is muscle tissue providing about 80% of the strength of artery wall 18. Thus the strength of resistance of adventitial layer 3 to any expansion of false lumen 31 between layers will cause expansion toward the artery true lumen 37 rather than expansion of adventitial layer 3. This fact is an important basis of the means of the invention revealed here for finding true lumen 37 from false lumen 31.

FIG. 4D is a side view of concentric steerable guidewires, one of larger size, making arcs of a curve within a large artery (aorta) to reach a puncture site in artery 10 (a coronary artery) where occlusion 7 with occlusion cap 8 is located (not to scale). Thus concentric steering guidewire are performing a function normally accomplished by Guide catheter having shapes with names such as Judkins and Amplatz. The stylet wire is not yet extended from J-tip guidewire 11 but will be at cap 8 is approached, just as it is in arteries peripheral to coronary arteries as shown in FIG. 4A.

FIG. 5 is a side view of advancing catheter 22 having a distal end and a proximal end with inside diameter slidably larger than outside diameter of J-tip guidewire 11 and having alternative configuration of either screw vanes 23 or screw grooves 9 on distal end. Advancing catheter 22 is has one OD from proximal to distal end rather than different ODs as used in prior art conventional catheter 24 that is used in prior art to advance loop of J-tip guidewire 11 within layers of artery wall 18 as shown in FIGS. 10, 12 and 13A.

FIG. 6A is a side view of stylet wire 16 having a distal end and proximal end made of stiff but flexible, resilient wire such as stainless steel which is sharp on distal end and made slidably smaller than inside diameter of J-tip guidewire 11 in which it is located with sharp end protruding or retracted. Stylet wire 16 serves several functions. First, being pointed on the distal end it aids in piercing layer 1, second it provides an axis for twisting J-tip guidewire 11 and advancing catheter 22 through the small stylet opening with the assistance of screw vanes 23 or screw grooves 9. Third, being somewhat stiff, stylet wire 16 can serve the stiffening function that is performed by the thickened portion of conventional catheter 24 as discussed with the aid of FIG. 12. The fourth function is to pierce layer 1 after false lumen 31 has been pushed into true lumen until their longitudinal axes are approximately parallel as described with FIGS. 15A-D.

FIG. 6B shows stylet wire 16 retracted in J-tip guidewire 11 by about the amount needed to form a loop of appropriate size in J-tip guidewire 11. J-tip guidewire 11 is manufactured with a biased J-shape tip and the J-tip takes the form of a loop when provided the proper stiffening and as it is pushed between layers of artery wall 18 to create a passageway called false lumen 31 which is intentionally dissected between layer 1 and layer 2 of artery wall 18 around occlusion 7.

FIG. 7 shows stylet wire 16 retracted in J-tip guidewire 11 by more than the amount needed to form a loop of appropriate size in J-tip guidewire 11. Also shown as an alternative configuration is advancing catheter 22 placed in about the position that does provide the appropriate amount of stiffening of J-tip guidewire 11 to make the proper size loop as shown. This loop is shown between layer 1 and layer 2 in FIG. 13A with the use of prior art and in FIG. 14 with the use of present device.

FIG. 8 shows tamping catheter 32, being a flexible tube having a distal end and proximal end with lumen therebetween and distal tamping balloon 34 located on distal end and a plurality of tamping balloons 5 located in series proximally to distal tamping balloon 34. Tamping balloons 5 are made of a combination of compliant material to allow expansion and non-compliant material to resist damage when tamping occlusion. Tamping catheter 32 can be advanced on J-tip guidewire 11 to perform the function that prior art conventional catheter 24 does by means of a larger OD in one section, i.e. stiffening J-tip guidewire 11 in addition to that stiffening provided by stylet wire 16 or advancing catheter 22. Distal tamping balloon 34 has a fluid inflation lumen located in wall of tamping catheter 32. This is the conventional location of fluid inflation lumens so is not shown in figures. Tamping balloons 5 have one common fluid inflation lumen also located in wall of tamping catheter 32. Tamping balloons 5 are shorter than balloons typically used for tamping from inside a subintimal false lumen 31 created by J-tip guidewire 11. This is because a series of shorter balloons provides a more uniform diameter of tamping force than does a long balloon when the entire series of a plurality of 34 is inflated from a common source of fluid pressure. Thus tamping is more quickly accomplished with a plurality of short tamping balloons 5.

FIG. 9A shows the alternative configuration of concentrically assembled tamping catheter 32, advancing catheter 22, J-tip guidewire 11 and stylet wire 16 all slightly extended beyond the distal end of the slidably larger component in which each is concentrically located. Being only slightly extended, the J-tip of guidewire 11 is constrained to a straight shape and it must be further extended to take the J shape and even further extended and constrained within tissue such as found between layers of an artery wall to assume the loop shape shown in FIGS. 13A and 14.

FIG. 9B shows the alternative configuration of concentrically assembled tamping catheter 32, J-tip guidewire 11 and stylet wire 16 all slightly extended beyond the distal end of the slidably larger component in which each is concentrically located. With advancing catheter eliminated in this configuration the sizes of concentric components are made so each is slidably larger than the one in its lumen.

FIG. 10 shows artery 10 with occlusion 7, occlusion cap 8 and 3 layers of artery wall 18 with prior art of conventional catheter 24, with J-tip guidewire 11 slidably located within, being pushed into artery wall 18 at intimal puncture site 29 which is at intersection of occlusion cap 8 and artery wall 18. J-tip guidewire 11 is straight because it is only slightly exposed outside the constraining environment of conventional catheter 24. Conventional catheter 24 has a "hipped" shape with thicker, less flexible, larger OD portion proximal to a thinner, more flexible distal portion. The occlusion is a deposit or degenerative accumulation of lipid-containing plaques on the innermost layer 1 of the artery wall 18. It may constitute a chronic total occlusion (CTO) meaning it has existed for some months as a 99% occlusion that cannot be crossed with a guidewire. A CTO occurs in about one-third of all cases and a guidewire is unable to enter, i.e. to cross a CTO, so a balloon cannot be introduced into the occlusion to push it aside. A CTO occlusion must be bypassed but any occlusion may be bypassed through artery wall 18.

FIG. 11 is a cross-sectional view of what is shown as a side view in FIG. 10, with occlusion 7 being shown as a CTO, but recognizing it is not necessary for it to be a CTO in order to make false lumen 31 between layers of artery wall 18.

FIG. 12 is a more detailed view of J-tip guidewire 11 in conventional catheter 24 which more clearly shows the thicker and thinner portions of prior art conventional catheter 24 needed to provide the proper stiffening for J-tip guidewire 11 to form the proper size loop.

FIG. 13A shows prior art where J-tip guidewire 11 has been pushed forward of conventional catheter 24 a distance that causes J-tip guidewire 11 to take the shape of a loop of correct size between layers 1 and 2 of artery wall 18. If pushed forward a greater distance than required the loop assumes a wider profile which is undesirable. The operator must be aware when the loop becomes too large and keep J-tip guidewire 11 forward of conventional catheter 24 the optimal distance for the optimal size loop. The subintimal passageway of false lumen 31 as shown here is short because of width of sheet but may be long in practice; 20 or 40 centimeters in length not being unusual.

As the length increases pressure on false lumen 31 increases making it more difficult for operator to manipulate prior art devices within false lumen 31. The prior art devices may be used in a retrograde procedure in which the false lumen 31 is made from arteries "downstream" to meet the false lumen 31 created by the antegrade movement. But the patient must be moved for a retrograde procedure and thus this is a complicating factor that requires extra time. With the present invention this pressure may be reduced by advancing steering guidewire 12 or tamping catheter 32 to distal end of advancing catheter 22 thus relieving pressure within false lumen on loop. What is not shown in any figure is that false lumen 31 tends to spiral around artery 10 as it progresses. Thus when J-tip guidewire 11 has reached the end of occlusion 7, as shown here, the X-Ray fluoroscopic device in the cath lab or operation room where the procedure is typically performed cannot determine in which direction true lumen 37 is from false lumen 31 where the spiraling ends.

FIG. 13B shows the means of re-entering 37 from false lumen 31 used in prior art inventions which are the basis of devices made by major medical device companies today. The means they use to pierce intimal layer 1 is to push a spear-shaped hollow needle 26 through side opening 35 in covering sheath 33 and through layer 1 distal to occlusion 7 at an angle pointed toward opposite artery wall 18. The prior art inventions do this after each has determined the correct direction by one of three different means. One prior art device uses radiopaque images that appear as different images from orthogonal X-Ray angles, another uses intravascular ultrasound (IVUS) images and the third inflates a balloon in healthy tissue distal to the occlusion to point hollow needle at opposite artery wall. The third may or may not use a hollow needle but it injures healthy tissue regardless of whether hollow needle is used or not. The invention revealed here uses a different means of identifying the direction of true lumen 37 from false lumen 31 and a different means of piercing layer 1 than that of prior art. The prior art devices work in a certain percentage of cases and when they do not, the procedure is terminated and the patient treated by open surgery to place a bypass graft around the occlusion.

Figure 13C:
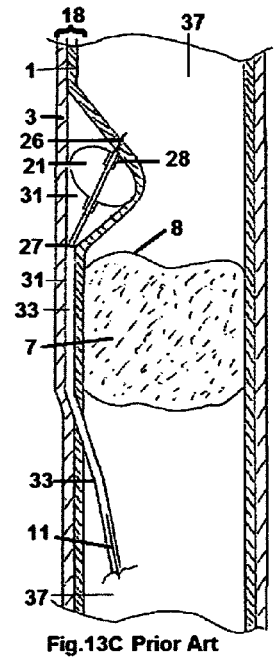
FIG. 13C shows a prior art device with one of two alternative shapes of inverted neck balloon that inflates in false lumen distal to occlusion to expand into true lumen.
Figure 13D:
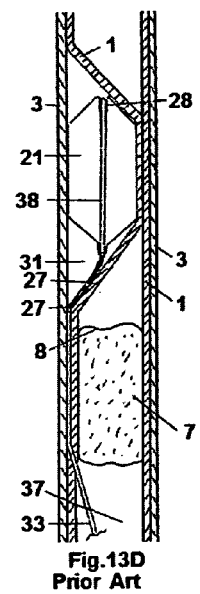
FIG. 13A shows prior art where J-tip guidewire has been pushed forward of conventional catheter a distance that causes J-tip guidewire take the shape of a loop of correct size between layers of artery wall.
FIG. 13 D shows an alternative configuration of prior art device shown in FIG. 13C in which inverted neck balloon is long and cylindrical.

FIG. 13C shows a prior art device with one of two alternative shapes of inverted neck balloon 21 that inflates in false lumen 31 distal to occlusion 7 to expand into true lumen 37. By inflating distal to occlusion 7, inverted neck balloon 21 is located in healthy tissue and its inflation destroys this healthy tissue and causes bleeding from all collaterals attached to that healthy tissue while leaving occlusion 7 intact. FIG. 13A shows the smaller of the two shapes of inverted neck balloons used in this prior art device, so it produces less damage than the larger inverted neck balloon shown in FIG. 13B. The neck is inverted so balloon catheter 38 does not extend beyond distal end of inverted neck balloon 21 which would cause balloon catheter 38 to be bent against layer 1 thus causing hollow needle 26 to be sent in a direction parallel to layer 1 rather than piercing through layer 1 when advanced by operator. Balloon catheter 38 must be constructed of such material in a way as to produce catheter bending 27 around occlusion 7, which produces some amount of weakness and difficulty in operator control of balloon catheter 38. This bending points hollow needle 26 at distal end of balloon catheter 38 toward opposite artery wall 18 at an angle that depends on the amount of inflation in inverted neck balloon 21 thus creating a source of increasing potential damage with increasing inflation should hollow needle 26 be advanced too far. Also increased inflation causes increased injury to healthy tissue by increasing size of inverted neck balloon 21. It is assumed that this prior art device is the basis for the "OffRoad®." device being produced by Boston Scientific.

FIG. 13 D shows an alternative configuration of prior art device shown in FIG. 13C. In this configuration inverted neck balloon 21 is longer and more cylindrical as well as larger than inverted neck balloon 21 shown in FIG. 13C. The object of larger cylindrical inverted neck balloon 21 is to cause intimal layer 1 to fully collapse toward opposite artery wall 18 thus pointing hollow needle 26 in a direction parallel to longitudinal axis of artery 10. This avoids the danger of pointing hollow needle 26 at opposite side of artery wall 18 as with the configuration shown in FIG. 13A. But this object is accomplished at the cost of detaching a larger section of healthy tissue and causing more collaterals to bleed than does the smaller size inverted neck balloon. It also causes a more acute bend in balloon catheter 38 which produces a greater amount of weakness and difficulty in operator control of balloon catheter 38 than does the alternative configuration shown in FIG. 13C.

FIG. 3E is a side view of prior art described in U.S. Pat. No. 8,241,311 in which cutting blade 40 is shown as extended from side of re-entry guidewire 39. The amount of extension is variable and cutting blade 39 has alternative configurations which may be retracted in re-entry guidewire 40.

FIG. 3F is a cross-section view of prior art cutting blade 40 extended from re-entry guidewire 39 in false lumen 31 between adventitial layer 3 and intimal layer 1. Cutting blade 39 is shown extended into layer 1 and the extent of extension is variable. The means this prior art device uses to find true lumen 37 from false lumen 31 is to rotate re-entry guidewire 360 degrees thus making a circumferential cut with blade 39. Since this cut is in all directions it must include the direction true lumen 37 is from false lumen 31. And since the extension of cutting blade 39 is variable intimal layer 1 may be cut entirely through or not by this circumferential cut. If intimal layer 1 is not completely severed this prior art device includes a balloon for enlarging the 360 degree opening to split the intimal layer. The device is described as being for re-entering true lumen 37 from a subintimal false lumen 31 thus no balloons are provided for tamping aside the occlusion, rather a stent is prescribed for opening the lumen to allow blood to flow. Being for re-entry, the prior art invention offers alternative means, such as a laser wire or a radiofrequency electrode to bore the false lumen and radiopaque elements to find the true lumen without describing how these alternatives achieve those objects or claiming them. Also discussed generally, but not claimed, is using re-entry guidewire 39 to create false lumen 31. Making circumferential cuts of less than 360 degrees are also described but the means used in this prior art device are not those of the present device so there is no further discussion.

Figure 14:
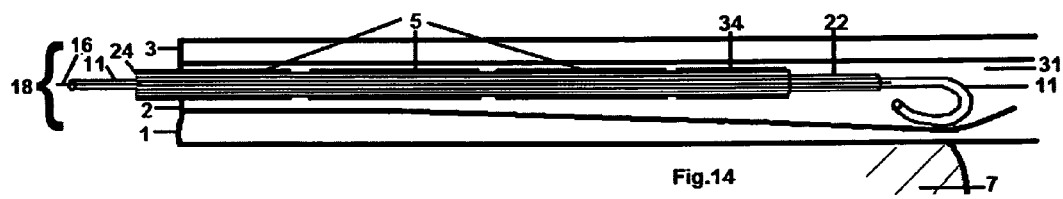
FIG. 14 shows the components of the invention revealed here as having differences from those used in prior art.

FIG. 14 shows the components of the invention revealed here as having differences from those used in prior art. Advancing catheter 22 used in the present invention has no thicker section as does prior art conventional catheter 24 because tamping catheter 32 or steering guidewire 12 serves the function of the larger diameter hipped section of prior art conventional catheter 24. Both steering guidewire 12 and tamping catheter 32 also can protect advancing catheter 22 and/or J-tip guidewire 11 from pressure encountered at the ends of long passageways. The steering function of steering catheter 12 may also be helpful to operator in certain situations. Components that pass through intimal puncture site 29 may be provided with alternative configurations of screw grooves 9 or screw vanes 23 to help introduce them through layer 1 when entry is difficult. The present invention is shown at the point in its use where false lumen 31 has been created to the distal end of occlusion 7 by the loop in J-tip guidewire 11 which is shown with stylet wire 16 inside and advancing catheter 22 outside, and with tamping catheter 32 around advancing catheter 22, and uninflated distal tamping balloon 34 and tamping balloons 5 attached to tamping catheter 32. Separate fluid lines are supplied in wall of tamping catheter 32 separately to distal tamping balloon 5 and the plurality of tamping balloons 5. It should be noted that no healthy tissue has been injured and that inflation of distal tamping balloon 34 at this point (or before) will not injure healthy tissue in artery wall 18 which lies distal to occlusion 7. Note: tamping catheter 32 may have been used to take pressure off of advancing catheter 22 by its presence which is of increasing importance as false lumen 31 becomes very long. Since tamping catheter 32 is to be employed at this point to accomplish re-entry from false lumen 31 to true lumen 37, its use to relieve pressure requires no additional operator action or time.

Figure 15A:
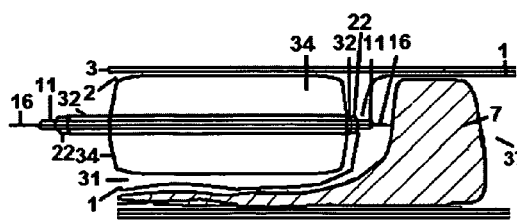
FIG. 15A shows the means used in the present invention for finding true lumen from false lumen by balloon inflation in tissue that is not in healthy tissue.

FIG. 15A shows the means used in the present invention for finding true lumen 37 from false lumen 31. Distal tamping balloon 34 is inflated at a point just proximal to that shown in FIG. 14, that is, where false lumen 31 is a short distance proximal to the point shown at the distal end of occlusion 7. The operator may choose the point at which to start pushing aside occlusion 7 and experience with the device will determine which is optimal as all options are possible with the device. Tissue in artery wall 18 is not healthy tissue where occlusion exists but immediately distal to occlusion 7 is healthy tissue with collateral vessels connected to that healthy tissue. It is important not to injure healthy tissue so it is desirable to make the entry from false lumen 31 to true lumen 37 in diseased tissue as present device does, in that way healthy tissue is not injured and the collateral vessels do not start to bleed. It is seen that inflation of distal tamping balloon 34 pushes aside a section of occlusion 7 and brings advancing catheter 22, J-tip guidewire 11 and stylet wire 16 approximately parallel with longitudinal axis of artery 10. If not as parallel as operator desires, operator may inflate tamping balloons 5 to any inflation level that brings about the desired parallel state and which causes a more gradual slope of bending on tamping catheter 32. The present device pierces layer 1 with stylet wire 16 along the longitudinal axis of artery 10 and thus does not endanger opposite wall by entering at an acute angle as do prior art devices. Since this angular pointing is dangerous at least one prior art device (see Pub No. 2007/0285596 and U.S. Pat. No. 6,217,527) reveals an automated control of the distance prior art hollow needle 26 can travel to ensure it does not penetrate artery wall 18. The present device avoids this dangerous situation by the means described. It may be noted that it is desirable, when using the present device, to administer the conventionally used bolus of heparin immediately after the introducing sheath is put in place after percutaneous entry. Advancing stylet wire 16 pierces layer 1 and advancing J-tip guidewire 11 makes the opening larger, with still larger opening achieved by advancing catheter 22. The opening of this size will probably cause layer 1 to tear open to a larger size as it is being stretched by inflation of distal tamping balloon 34. If the desired state of layer 1 being torn open is not achieved, distal tamping balloon 34 is uninflated and advanced to position shown in FIG. 15B.

Figure 15B:
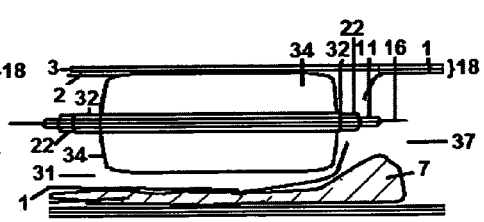
FIG. 15 B shows the state that exists when occlusion is almost completely tamped aside and intimal layer is open.
FIG. 15C shows the state that exists when occlusion is completely pushed aside with intimal layer wrapped around it.
FIG. 15D is a longitudinal view of occlusion wrapped in intimal layer tamped to the side of artery before J-tip guidewire is removed.

FIG. 15B shows the state that exists either after that shown in FIG. 15A or immediately after the state shown in FIG. 14B, namely that occlusion is almost completely tamped aside and layer 1 open. Operator will observe X-Ray fluoroscopic images to decide if the occlusion is completely pushed aside at distal end of occlusion and if not will again deflate balloons and advance tamping catheter 32. In short occlusions where tamping balloons 5 have been inflated in such a way as to have opened the entire extent of occlusion 7, blood will flow when tamping balloons 5 are uninflated.

Figure 15C:
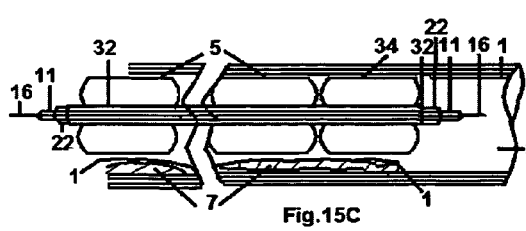

FIG. 15C shows the state that exists when occlusion 7 is completely pushed aside with layer 1 wrapped around crushed occlusion 7 and all tamping balloons 5 on distal tamping balloon 34 inflated. In long occlusions tamping balloons 5 are deflated and moved to increasingly proximal positions and there inflated until entire length of occlusion is tamped to the side wrapped in layer 1. The fact that a plurality of tamping balloons 5 are used rather than one tamping balloon reduces the amount of time required to tamp long occlusions and does so with a consistency of pressure on occlusion not achievable with the single tamping balloon usually used in prior art devices. It is also shown that in addition to using distal tamping balloon 34 balloon to push aside the occlusion, tamping balloons 5 on tamping catheter 32 may also be used to assist distal tamping balloon 34 to ensure that stylet wire 16 emerges from advancing catheter 22 approximately parallel to the longitudinal axis of true lumen 37 in artery 10 and not pointed toward opposite artery wall 18 as in all prior art devices.

Figure 15D:
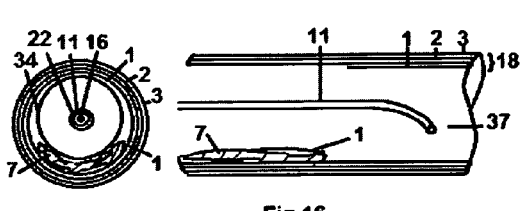

FIG. 15D is a longitudinal view of occlusion 7 wrapped in layer 1 tamped to the side of artery 10 before device is removed from body.

Figure 16:
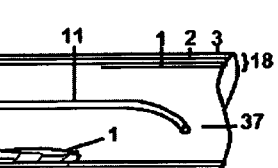
FIG. 16 is side view of J-tip guidewire left in artery after tamping which has pushed occlusion 7 aside and placed intimal layer around occlusion.

FIG. 16 is a side view of J-tip guidewire 11 left in artery 10 after tamping has pushed aside occlusion 7 with layer 1 around it to allow blood to flow. It is important for J-tip guidewire not to be removed with other device components if a subsequent percutaneous procedure is to be performed that allows some type of graft tube or stent graft to be placed concentrically in this previously occluded segment of artery

The invention claimed is:

1. A device for bypassing an occlusion located in an artery true lumen by means of inserting a J-tip guidewire and stylet wire assembly through an intimal layer of a wall of said artery proximate said occlusion and pushing said J-tip guidewire forward of and with said stylet wire located in a portion of said J-tip guidewire so as to dissect a false lumen between said intimal layer and a medial layer of said wall around said occlusion and deploying a tamping balloons and tamping catheter assembly in said false lumen and inflating said tamping balloons to crush and push aside said intimal layer and said occlusion causing axes of said false lumen and said true lumen to coincide with said intimal layer straight ahead of said stylet wire thus allowing said intimal layer to be safely pierced by said stylet wire for blood to flow from said true lumen, through said false lumen, and into said true lumen thus bypassing said occlusion, comprising: a J-tip guidewire and stylet wire assembly having structure and materials such that said J-tip guidewire is sufficiently flexible to bend in direction opposite to encountered resistance and said stylet wire being straight and sufficiently stiff to prevent any portion of said J-tip guidewire occupied by said stylet wire from deviating from said straight shape of said stylet wire, thus when said stylet wire completely occupies said J-tip guidewire and is pushed against an intimal layer of a wall of an artery said J-tip guidewire will pass through said intimal layer and pushing said J-tip guidewire forward of said stylet wire will cause said J-tip guidewire to bend away from encountered resistance from a medial layer of said wall and further advancement of said J-tip guidewire forward of said stylet wire will cause said J-tip guidewire to bend away from encountered resistance between said intimal layer and said medial layer in a J-shape which also separates said intimal layer from said medial layer in said J-shape and further pushing forward of said J-tip guidewire will cause said J-tip guidewire to bend away from encountered resistance in a loop shape between said intimal layer and said medial layer and pushing said J-tip guidewire and stylet wire assembly forward causes said loop shape to dissect said intimal layer from said medial layer to form a false lumen in said artery wall around said occlusion, wherein said J-tip guidewire comprises a coil of wire having a proximal end, a distal end, and a lumen therebetween, wherein said distal end is biased in the shape of a J and is configured to bend in a direction opposite to a direction of resistance encountered in any portion of said J-tip guidewire that is not occupied by a straight stylet wire that restrains the occupied portion from flexing, and wherein said stylet wire comprises a proximal end, a distal end, and a straight unbiased wire therebetween having a size capable of sliding in said lumen of said J-tip guidewire and being of a structure and being made of a material that makes said stylet wire sufficiently stiff such that when positioned within any portion of said lumen of said J-tip guidewire, said portion conforms to the straight shape of said stylet wire, thereby restraining said portion of said J-tip guidewire from flexing or being in any shape other than that of said straight unbiased wire of said stylet, and having a distal end being sharp; a tamping balloons and tamping catheter assembly adapted for deployment over said guide wire and stylet assembly into said false lumen and being of a structure and made with materials having characteristics such that inflating said tamping balloons in said false lumen causes said occlusion to be crushed and pushed aside into said true lumen along with said intimal layer thus approximately aligning axes of said true lumen and said false lumen, wherein said tamping catheter of said tamping balloons and tamping catheter assembly comprises a distal end, a proximal end, and a lumen therebetween being slidably larger than said J-tip guidewire, and having standard fluid supply lines and no other openings in a wall of said tamping catheter, wherein said tamping balloons of said tamping balloons and tamping catheter assembly comprise a plurality of tamping balloons made of a combination of compliant and non-compliant materials and being mounted contiguously around said tamping catheter from a distal tamping balloon mounted on said distal end of said tamping catheter and having a separate fluid supply line to said plurality of tamping balloons mounted proximally to said distal tamping balloon having a common fluid supply line, and further comprising a deflated state circumference slightly larger than that of said false lumen and an inflated state circumference slightly smaller than that of said true lumen, whereby said J-tip guidewire and stylet wire assembly is configured to be advanced to puncture said intimal layer of said artery wall proximate said occlusion as said stylet wire provides axis for rotation of said J-tip guidewire to ease it through said intimal layer puncture and pushing said J-tip guidewire ahead of said stylet wire causing a distal portion of said J-tip guidewire to be unoccupied by said stylet wire thus allowing said distal portion of said J-tip guidewire to bend in a direction away from resistance encountered to form said J-shape and further pushing saucer, causing said J-shape to further bend into a loop shape that dissects said intimal layer from said medial layers of said artery wall around said occlusion to form said false lumen into which is introduced said tamping balloons and tamping catheter assembly where said distal tamping balloon on said distal end of said tamping catheter is partially made of compliant material, and is configured to be inflated causing false lumen to be pushed into true lumen with approximate parallel alignment of their axes so said stylet wire can be safely advanced straight ahead to pierce said intimal layer stretched in front of said distal tamping balloon, and said plurality of tamping balloons, being partially made of non-compliant material which resists damage when crushing and pushing aside said occlusion wrapped in said intimal layer whereupon said device is configured to be removed from the body with possible exception of J-tip guidewire which may be needed for a subsequent procedure; and two clamp arcs in the shape of a rigid ring of rectangular cross-section cut in two halves each slightly less than 180 degrees of arc with an inner circumference of said rigid ring being same as outer circumference of said handle and said steering catheter with said two clamp arcs having a protruding tapered nib on the, inner circumference for extending between said handle and said steering catheter, wherein said tapered nib having a cross-section tapering from a V-shape to a rectangular shape along said circumference; ribbed receivers being cavities in ends of each end of each of said halves of said clamp arcs that are in the zigzag shape of ribs on an antique washboard; and ribbed wafers in the zigzag shape of ribs on an antique washboard that fit in said ribbed receivers, whereby said ribbed wafers in ribbed receivers are configured to hold said halves of said clamp arcs together and interlacing said ribbed receivers and said ribbed wafers ribs keeps halves locked at any angle of rotation operator rotates said halves until an operator overcomes a previous locked position by another rotation, thus making the width of separation of said handle from said steering guidewire equal to the width of said tapered nib at any given degree of rotation of said halves of said clamp arcs.

2. The device of claim 1, further comprising: a steering guidewire made of wire coiled on a mandrel, having a distal end, a proximal end, and a lumen therebetween, having an inside diameter slidably larger than an outside diameter of a component to be slidably contained within including said J-tip guidewire and stylet wire assembly; and a handle being a short section of said steering guidewire separate from but held against said proximal end of said steering guidewire by a ribbon wire, wherein said ribbon wire has a proximal end, a distal end and a thin rectangular wire therebetween with said proximal end attached inside said handle and said ribbon wire proceeding distally into said lumen of said steering guidewire to a ribbon exit between adjacent coils of wire in said steering guidewire and after exiting said lumen then proceeding outside said steering guidewire to a ribbon attachment outside on said distal end of said steering guidewire, whereby the action of an operator pulling on said handle while holding said steering guidewire in place causes said ribbon wire to shorten by incrementally variable amounts between the segment of said steering guidewire located between said ribbon exit and said ribbon attachment at said distal end thus causing said segment to curve in an arc variably proportional to the extent chord of arc, is shortened by shortening said ribbon wire.

3. The device of claim 1, further comprising: one or more larger steering guidewires each being of slidably larger circumference than the other and the smallest being of slidably larger circumference than said guidewire and stylet assembly and each said one or more steering guidewires being rotatable through 360 degrees within the other, wherein said one or more larger steering guidewires is made of wire coiled on a mandrel, having a distal end, a proximal end, and a lumen therebetween, and wherein said one or more larger steering guidewires comprises a handle separate from but held against said one or more larger steering guidewires by a ribbon wire, and said ribbon wire having a proximal end, a distal end and a thin rectangular wire therebetween with said proximal end attached at a ribbon attachment inside said handle and said ribbon wire proceeding distally into said lumen of said steering guidewire to a ribbon exit between adjacent coils of wire in said steering guidewire and exiting said lumen then proceeding outside said steering guidewire to a ribbon attachment outside on said distal end of said one or more steering guidewires, configured such that an operator can use one or more of said larger steering guidewires to point said steering guidewire in any one of 360 degrees of rotation while another of said one or more steering guidewire is pointed in any one of the same or different plane of 360 degrees of rotation in order to provide acute complex angles needed to reach hard-to-access points such as a non-convex occlusion or sharp turn in an artery.

4. The device of claim 1, further comprising: an advancing catheter comprising a tube having a proximal end, a distal end, and a lumen therebetween with an inner diameter slidably larger than said J-tip guidewire and outside diameter slidably smaller than an inner diameter of said tamping catheter and being made of material sufficiently stiff to impose a shape of said advancing catheter on any portion of said J-tip guidewire over which said advancing catheter is located, whereby said advancing catheter imposes its straight shape over portion of said J-tip guidewire located in said advancing catheter allowing said J-tip guidewire to form the proper size loop to dissect said false lumen, and may be advanced over said J-tip guidewire to relieve resistance pressure on said J-tip guidewire when encountered in long occlusions.

5. The device of claim 4, further comprising:
a plurality of screw grooves in the shape of short grooves of about 1-3 mm pitched at a slight angle and cut on said distal end of said J-tip-guidewire, said advancing catheter, and said tamping catheter, whereby said plurality of screw grooves are configured to assist entry of said J-tip guidewire, said advancing catheter, and said tamping catheter by urging them through said intimal layer when pushed against said intimal layer and twisted.

6. The device of claim 4, further comprising:
a plurality of screw vanes in the shape of short, low profile vanes of about 1-3 mm pitched at slight angles being located on said distal end of said J-tip guidewire and on said advancing catheter, and said tamping catheter, whereby said screw vanes are configured to assist entry of said J-tip guidewire, said advancing catheter, and said tamping catheter by urging them through said intimal layer when pushed against said intimal layer and twisted.

* * * * *